(12) United States Patent
Kim

(10) Patent No.: US 11,338,108 B2
(45) Date of Patent: May 24, 2022

(54) SLEEP SYSTEM AND SLEEP-INDUCING DEVICE USING CARBON DIOXIDE

(71) Applicant: NYX INC., Seoul (KR)

(72) Inventor: Dong Sin Kim, Seoul (KR)

(73) Assignee: NYX INC., Seoul (KR)

( * ) Notice: Subject to any disclaimer, the term of this patent is extended or adjusted under 35 U.S.C. 154(b) by 0 days.

(21) Appl. No.: 17/334,733

(22) Filed: May 29, 2021

(65) Prior Publication Data

US 2021/0283366 A1    Sep. 16, 2021

Related U.S. Application Data

(63) Continuation of application No. PCT/KR2020/001108, filed on Jan. 22, 2020.

(30) Foreign Application Priority Data

Jan. 28, 2019  (KR) .................. 10-2019-0010359
Oct. 18, 2019  (KR) .................. 10-2019-0130150

(51) Int. Cl.
*A61M 21/02*   (2006.01)
*A61M 16/10*   (2006.01)
(Continued)

(52) U.S. Cl.
CPC ........ *A61M 21/02* (2013.01); *A61M 16/1005* (2014.02); *A61M 16/122* (2014.02);
(Continued)

(58) Field of Classification Search
CPC ............ A61M 16/1005; A61M 16/122; A61M 2016/103; A61M 21/02; A61M 2021/0077; A61M 2202/0225
See application file for complete search history.

(56) References Cited

U.S. PATENT DOCUMENTS 4,905,688 A * 3/1990 Vicenzi ................. A61M 16/00
                                                   128/201.25
7,018,443 B2 * 3/2006 Kutt ....................... A63B 23/18
                                                   95/8
(Continued)

FOREIGN PATENT DOCUMENTS

JP            07225042 A    8/1995
JP       2006-014729 A    1/2006
(Continued)

OTHER PUBLICATIONS

International Search Report of PCT Application No. PCT/KR2020/001108 dated May 7, 2020.
(Continued)

*Primary Examiner* — Justine R Yu
*Assistant Examiner* — Matthew D Ziegler
(74) *Attorney, Agent, or Firm* — Maschoff Brennan

(57) ABSTRACT

The present invention relates to a sleep-inducing system using carbon dioxide. The sleep-inducing system includes a mixed gas generation unit which generates a mixed gas of which a carbon dioxide concentration is within a preset range by mixing provided carbon dioxide and air, an emission unit which sprays the mixed gas from a position spaced apart from a user's face, a concentration sensing sensor which measures the carbon dioxide concentration of the sprayed mixed gas, and a control unit which controls the carbon dioxide concentration of the mixed gas generated by the mixed gas generation unit to be within the preset range on the basis of the measured carbon dioxide concentration.

14 Claims, 11 Drawing Sheets

(51) Int. Cl.
   *A61M 16/12*   (2006.01)
   *A61M 21/00*   (2006.01)
(52) U.S. Cl.
   CPC .............. *A61M 2016/103* (2013.01); *A61M 2021/0077* (2013.01); *A61M 2202/0225* (2013.01)

(56) References Cited

U.S. PATENT DOCUMENTS

| | | | | |
|---|---|---|---|---|
| 7,487,646 | B2* | 2/2009 | Matsushima | A47C 19/005 236/49.3 |
| 10,226,591 | B1* | 3/2019 | Tarler | A61M 16/122 |
| 10,231,864 | B1* | 3/2019 | Webster | A61B 5/4836 |
| 10,898,669 | B2* | 1/2021 | Luo | A61B 5/291 |
| 2003/0188743 | A1* | 10/2003 | Manne | A62B 18/003 128/201.22 |
| 2004/0144383 | A1 | 7/2004 | Thomas et al. | |
| 2004/0255939 | A1 | 12/2004 | Feldman | |
| 2005/0217674 | A1 | 10/2005 | Burton et al. | |
| 2006/0079170 | A1* | 4/2006 | Schmid | F24F 1/0073 454/187 |
| 2006/0185673 | A1 | 8/2006 | Critzer et al. | |
| 2007/0084463 | A1* | 4/2007 | Niemann | A61M 16/06 128/201.25 |
| 2008/0078397 | A1* | 4/2008 | Scott | A61M 16/08 128/205.25 |
| 2008/0308106 | A1* | 12/2008 | Augustine | A47C 7/744 128/205.29 |
| 2013/0296812 | A1* | 11/2013 | Bangera | A61B 18/0218 604/290 |
| 2017/0333664 | A1 | 11/2017 | Luo et al. | |

FOREIGN PATENT DOCUMENTS

| | | | |
|---|---|---|---|
| KR | 2020000007882 | U | 5/2000 |
| KR | 10-2008-0096965 | A | 11/2008 |
| KR | 10-2010-0129489 | A | 12/2010 |
| KR | 10-1055518 | B1 | 8/2011 |
| KR | 10-2012-0108491 | A | 10/2012 |
| KR | 10-1725877 | B1 | 4/2017 |
| KR | 10-2017-0123534 | A | 11/2017 |
| KR | 10-2019-0066268 | A | 6/2019 |

OTHER PUBLICATIONS

Written Opinion of PCT Application No. PCT/KR2020/001108 dated May 7, 2020.
International Search Report of PCT Application No. PCT/KR2020/015013 dated Apr. 21, 2021.
Written Opinion of PCT Application No. PCT/KR2020/015013 dated Apr. 21, 2021.
KR Notice of Allowance of Korean Patent Application No. 10-2019-0130150 dated Jun. 8, 2020.
KR Notice of Allowance of Korean Patent Application No. 10-2020-0094110 dated Jan. 18, 2021.

* cited by examiner

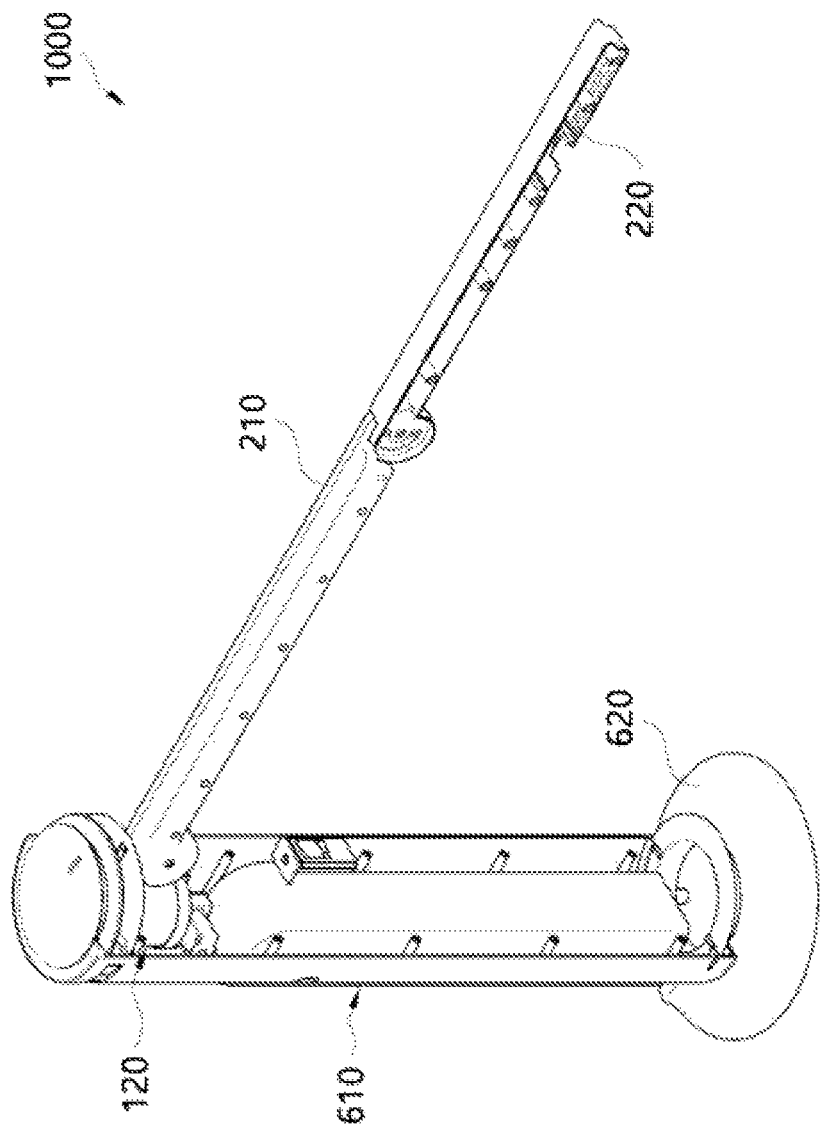

SLEEP SYSTEM AND SLEEP-INDUCING DEVICE USING CARBON DIOXIDE

TECHNICAL FIELD

The present invention relates to a sleep system and a sleep-inducing device using carbon dioxide.

BACKGROUND ART

Insomnia symptoms caused by stress are spreading throughout society. The insomnia symptoms include not only a symptom of not being able to get a deep sleep, but also a symptom of sleep disturbance such as a difficulty in maintaining a sleeping condition, lack of a sleep time or not feeling easily recovered even after waking up, and the like.

In a case in which the insomnia symptoms persist, fatigue, decreased concentration, mood disorders, pain, dysfunction in daily life, and the like are caused, and as the insomnia symptoms persist for a long time, an incidence rate of disease increases.

As a measure for clearing up such insomnia symptoms, taking sleeping pills is widely known. The sleeping pill exerts a strong impact on a specific receptor of a brain to induce sleep, which essentially serves a sedative-like function.

The sleeping pill may aid in immediate sleep, but when the sleeping pill is taken frequently, a tolerance develops, and a higher dose of the sleeping pill should be taken. In a case in which the taking of the sleeping pills is stopped, a side effect of worsening of the insomnia symptoms may occur.

Accordingly, devices which induce sound sleep by building external environments for inducing sleep without affecting the human body are recently being developed.

Meanwhile, a fact is widely known that a high concentration of carbon dioxide in a closed space causes drowsiness, and it may be confirmed by US air quality standards that drowsiness is induced at a concentration of carbon dioxide which is greater than or equal to 2,000 ppm.

Technical Problem

The present invention is directed to providing a sleep-inducing system capable of inducing sleep by momentarily increasing a carbon dioxide concentration of air inhaled by a user having difficulty in sleeping.

The present invention is directed to providing a sleep-inducing device capable of inducing sleep by momentarily increasing a carbon dioxide concentration of air inhaled by a user having difficulty in sleeping.

Technical Solution

One aspect of the present invention provides a sleep-inducing system using carbon dioxide including a mixed gas generation unit which generates a mixed gas of which a carbon dioxide concentration is within a preset range by mixing provided carbon dioxide and air, an emission unit which sprays the mixed gas from a position spaced apart from a user's face, a concentration sensing sensor which measures the carbon dioxide concentration of the sprayed mixed gas, and a control unit which controls the carbon dioxide concentration of the mixed gas generated by the mixed gas generation unit to be within the preset range on the basis of the measured carbon dioxide concentration.

The preset range of the carbon dioxide concentration may be 30,000 to 100,000 ppm in a mixing unit of the mixed gas generation unit and 15,000 to 25,000 ppm in an inhalation system of the user.

The mixed gas generation unit may include a providing unit which provides the carbon dioxide, a mixing unit which mixes the carbon dioxide received from the providing unit and the air to generate the mixed gas, and a storage unit which stores the mixed gas, and the control unit may control a flow rate of the carbon dioxide provided from the providing unit to the mixing unit or a flow rate of external air to control the carbon dioxide concentration of the mixed gas.

The providing unit may have a structure detachably connected to the mixing unit.

The emission unit may include a flow channel unit which provides a moving channel of the mixed gas and a spraying unit including at least one nozzle through which the mixed gas received through the flow channel unit is sprayed toward the user's face, and the flow channel unit may have a stretchable or shape-changeable structure to control a spacing distance between the nozzle and the user's face.

A distance sensing sensor which measures the distance between the nozzle and the user's face may be provided at one side of the nozzle, and the control unit may set a range of the carbon dioxide concentration of the mixed gas on the basis of a signal of the measured distance.

The concentration sensing sensor may be provided at one side of the spraying unit or one portion of the flow channel unit.

The sleep-inducing system using carbon dioxide may further include a sleeping status detecting sensor which detects a sleeping status of the user, the sleeping status detecting sensor may detect the sleeping status of the user after the mixed gas is sprayed for a preset time, and the control unit may stop the spray of the mixed gas when a signal of the detected sleeping status is received and the user in a sleep state is determined and may extend a spray time of the mixed gas when the user not in the sleep state is determined. However, the total sum of the spray times may be restricted within a predetermined range.

The sleep-inducing system using carbon dioxide may further include a purification unit which stores solid oxygen for decreasing the concentration of the carbon dioxide of the sprayed mixed gas and includes a diffusion fan for widely spreading the solid oxygen around the user, and the control unit may spread the solid oxygen around the user by driving the diffusion fan of the purification units when the spray of the mixed gas is completed.

The control unit may include a communication unit which transmits and receives a data signal to and from an external device, and the control unit may set a range of the carbon dioxide concentration of the mixed gas according to the signal received from the external device.

Another aspect of the present invention provides a sleep-inducing device using carbon dioxide including an external air inflowing unit which receives external air from the outside, a providing unit which is disposed under the external air inflowing unit and supplies carbon dioxide, a mixing unit which is disposed between the external air inflowing unit and the providing unit and mixes the carbon dioxide received from the providing unit and the air to generate a mixed gas of which a carbon dioxide concentration is within a preset range, and an emission unit receives the mixed gas from the mixing unit, and sprays the mixed gas from a position spaced apart from a user's face.

The preset range of the carbon dioxide concentration may be 30,000 to 100,000 ppm in the mixing unit and 15,000 to 25,000 ppm in an inhalation system of the user.

The providing unit may have a structure detachably connected to the mixing unit.

The emission unit may include a flow channel unit which is connected to the mixing unit and provides a flow channel of the mixed gas and a spraying unit including at least one nozzle through which the mixed gas received through the flow channel unit is sprayed toward a user's face.

The flow channel unit may be stretchable or shape-changeable to control a spacing distance between the spraying unit and the user's face.

The emission unit may further include a distance sensing sensor which measures the distance between the spraying unit and the user's face.

The sleep-inducing device using carbon dioxide according to one embodiment of the present invention may further include a housing which accommodates the providing unit and the mixing unit therein and a fixing unit which is connected to the housing and fixes the sleep-inducing device.

Advantageous Effects

A sleep-inducing system using carbon dioxide according to the present invention mixes carbon dioxide and air to generate a mixed gas, of which a concentration of the carbon dioxide is within a preset range, and momentarily increase a carbon dioxide concentration of air inhaled by a user having difficulty in sleeping by spraying the mixed gas at a position spaced apart from a user's face for a predetermined time so that sleep of the user can be induced.

A sleep-inducing device using carbon dioxide according to the present invention mixes carbon dioxide and air to generate a mixed gas of which a concentration of the carbon dioxide is within a preset range and momentarily increases a carbon dioxide concentration in air inhaled by a user having difficulty in sleeping by spraying the mixed gas at a position spaced apart from a user's face for a predetermined time so that sleep of the user can be induced.

DESCRIPTION OF DRAWINGS

FIG. 9 is a perspective view in which a portion of a housing is removed from the sleep-inducing device using carbon dioxide according to one embodiment of the present invention to observe an interior thereof.

MODES OF THE INVENTION

Figure 1:
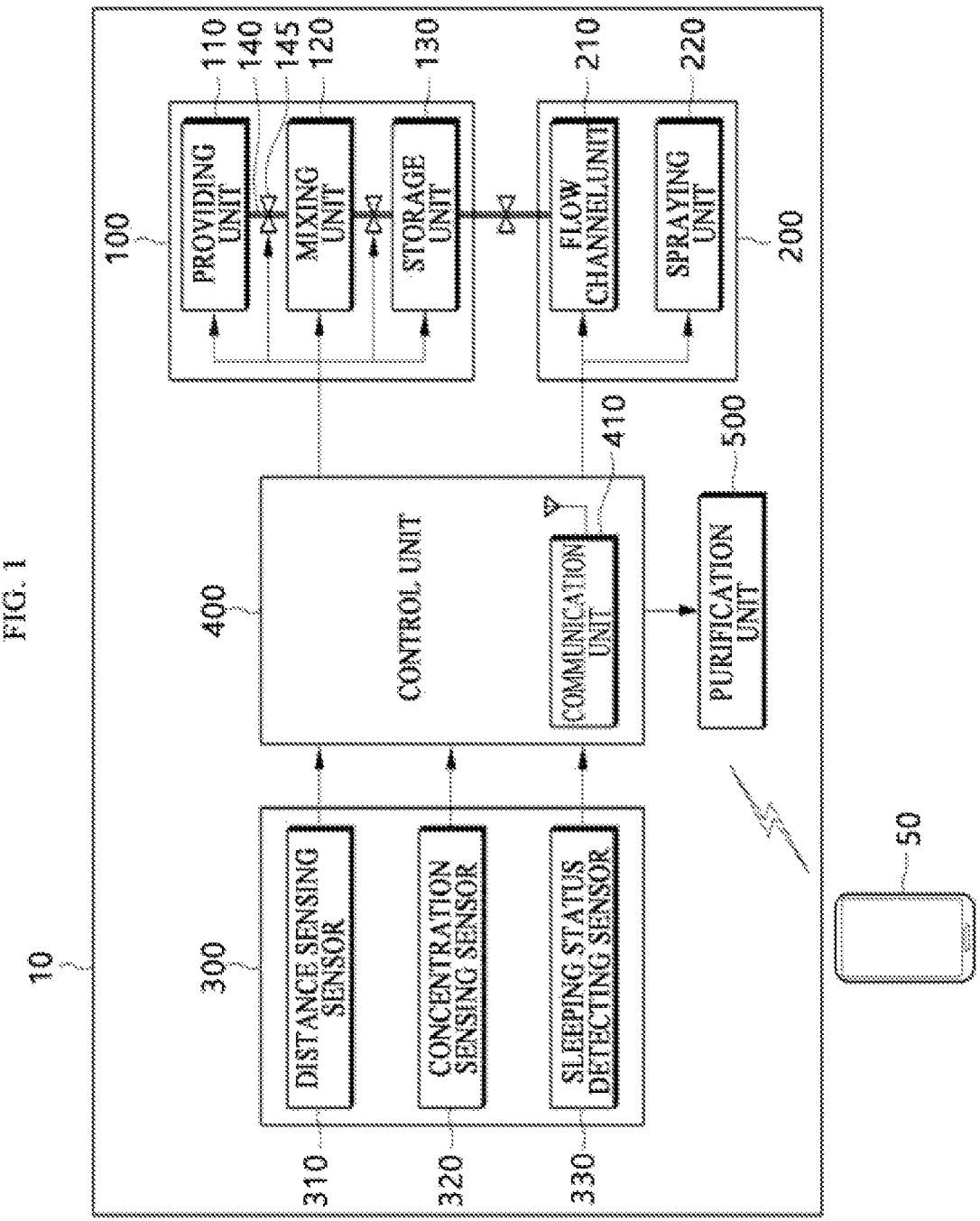
FIG. 1 is a schematic block diagram illustrating a sleep-inducing system using carbon dioxide according to one embodiment of the present invention.

Hereinafter, embodiments of the present invention will be described in detail with reference to the accompanying drawings in order for those skilled in the art to easily implement the present invention. However, the present invention may be implemented in several different forms and is not limited to the embodiments described herein. Parts irrelevant to descriptions are omitted in the drawings in order to clearly explain the present invention, and the same or similar parts are denoted by the same reference numerals throughout this specification.

Throughout this specification, when a part is referred to as being "connected" to another part, it includes being "directly connected" to another part and "indirectly connected" to another part with still another part disposed therebetween.

In addition, when a certain part "includes" a certain component, this does not exclude other components unless explicitly described otherwise, and other components may in fact be included.

Spatially relative terms such as "below," "beneath," "lower," "above," "upper," and the like may be used to more easily describe a relationship between one element and another element as illustrated in the drawings. The spatially relative terms should be understood to have directions as illustrated in the drawings and have other directions when the elements are used or operated. For example, when an upside of an element illustrated in the drawing is turned downward, the element which is illustrated to be present below or beneath another element may be present above another element. Accordingly, the term "below" may be used as an example including both a downward direction and an upward direction. An element may be arranged in another direction, and thus, the spatially relative terms may be interpreted based on an arrangement direction.

FIG. 1 is a schematic block diagram illustrating a sleep-inducing system using carbon dioxide according to one embodiment of the present invention.

Referring to FIG. 1, a sleep-inducing system 10 using carbon dioxide according to one embodiment of the present invention may include a mixed gas generation unit 100, an emission unit 200, a sensor unit 300, and a control unit 400.

The mixed gas generation unit 100 according to one embodiment of the present invention may mix carbon dioxide ($CO_2$) and air, which are being supplied, to generate a mixed gas of which a concentration of the carbon dioxide is within a preset range.

The mixed gas generation unit 100 may include a providing unit 110 for providing the carbon dioxide, a mixing unit 120 for receiving the carbon dioxide from the providing unit 110 and generating the mixed gas, and a storage unit 130 for storing the mixed gas.

The providing unit 110 may store carbon dioxide therein and supply the carbon dioxide to the mixing unit 120.

For example, the providing unit 110 may be a gas tank, a gas cylinder, or a chamber capable of storing high-pressure gas.

The providing unit 110 may include radio-frequency identification (RFID). Accordingly, it may be determined whether the providing unit 110 is suitable to be used in the sleep-inducing system 10 using carbon dioxide according to one embodiment of the present invention, for example, whether the providing unit 110 is a genuine product.

The providing unit 110 may exhaust carbon dioxide stored therein while supplying the carbon dioxide. Accordingly, in a case in which the providing unit 110 is a disposable unit, the providing unit 110 may have a structure detachably or separably connected to the mixing unit 120 so that the providing unit 110 is replaceable. In addition, in a case in which the providing unit 110 is a rechargeable multi-use unit, the providing unit 110 may have a structure into which carbon dioxide is injectable.

The providing unit 110 may be connected to the mixing unit 120 through a tube 140 for supplying the carbon dioxide, and a valve 145 for controlling a flow rate of the carbon dioxide is provided on the tube 140 to control opening or closing of the tube 140.

For example, the valve 145 may be a solenoid valve of which opening or closing is electronically controlled by the control unit 400, and the control unit 400 may control an opening degree of the valve 145 to control the flow rate of the carbon dioxide supplied to the mixing unit 120.

The mixing unit 120 may receive carbon dioxide from the providing unit 110, mix the received carbon dioxide and air to generate a mixed gas of which a carbon dioxide concentration is within the range of 30,000 to 100,000 ppm or the range of 3 to 10% in the mixing unit, and within the range of 15,000 to 25,000 ppm or the range of 1.5 to 2.5% in a user's inhalation system.

According to a test result in an autonomous manner, it was seen that, in a case in which a concentration of the carbon dioxide is within the range of 1.5 to 2.5% in the user's inhalation system, drowsiness of the user is induced so that sleeping is inducible.

According to one embodiment of the present invention, the mixed gas of which the concentration of the carbon dioxide is within the range of 30,000 to 100,000 ppm or the range of 3 to 10% in the mixing unit 120 is generated in consideration that the concentration may be reduced due to diffusion in a process in which the mixed gas is provided to or sprayed on the user's face so that the mixed gas of which a carbon dioxide concentration is within the range of 1.5 to 2.5 may be provided to the user's face spaced apart from a spraying unit 220 by 14 to 21 cm.

The sleep-inducing system 10 using carbon dioxide according to one embodiment of the present invention generates a mixed gas within the range of TWA-5,000/STEL-30,000 which is a carbon dioxide exposure safety concentration (hereinafter, "safety concentration") specified by the U.S. Occupational Safety and Health Administration and governments around the world including the Republic of Korea. The term "TWA-5,000" denotes that the exposure time should be less than or equal to eight hours at an average of 5,000 ppm or less, and the term "STEL-30,000" denotes that the exposure time should be less than or equal to 15 minutes at 30,000 ppm.

That is, the mixing unit 120 of the sleep-inducing system 10 using carbon dioxide according to one embodiment of the present invention generates a mixed gas within the safe concentration range. In addition, the sleep-inducing system 10 using carbon dioxide according to one embodiment of the present invention may provide the mixed gas to the user through the emission unit 200 to control the concentration around a user's respiration system to be within the safe concentration range and also provide an optimized sleep environment to the user.

The storage unit 130 may store the mixed gas generated by the mixing unit 120. For example, the storage unit 130 may be formed to have a housing structure in which a storage space is provided to accommodate or store the mixed gas. The storage unit 130 and the mixing unit 120 may be integrally formed.

Figure 2:
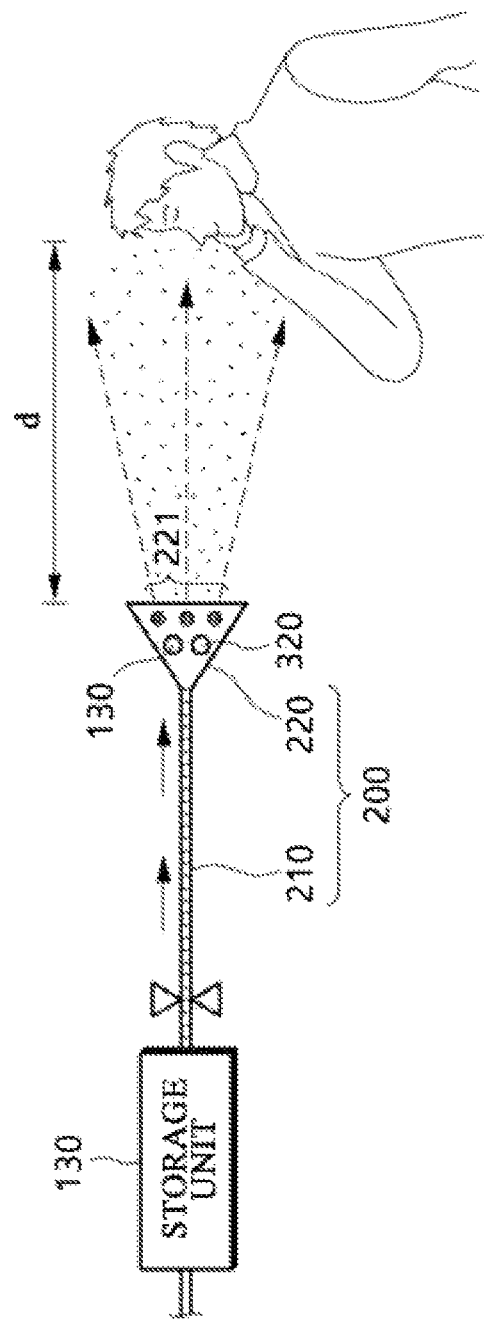
FIG. 2 is a schematic view illustrating a state in which a mixed gas is sprayed onto a user through an emission unit according to one embodiment of the present invention.
Figure 3:
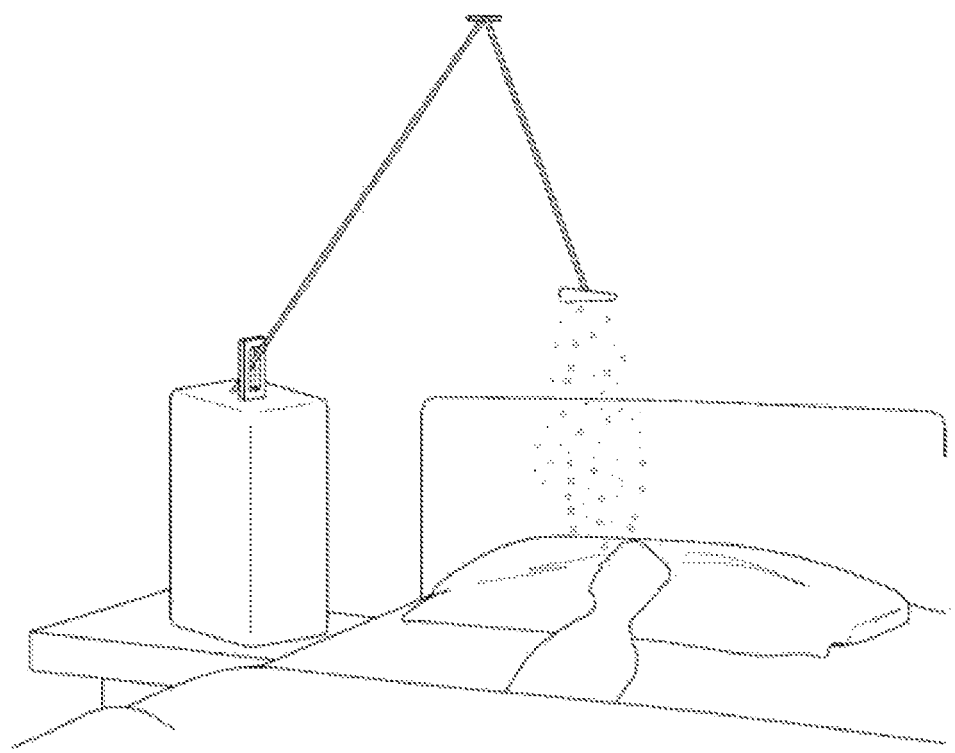
FIG. 3 is a schematic usage view according to one embodiment of the present invention.

FIG. 2 is a schematic view illustrating a state in which the mixed gas is sprayed onto the user through the emission unit according to one embodiment of the present invention.

Referring to FIGS. 1 and 2, the emission unit 200 according to one embodiment of the present invention may spray the mixed gas received from the storage unit 130 from a position spaced apart from the user's face by a preset distance d.

For example, the emission unit 200 may spray the mixed gas on the user's face in at least one manner among a contact spray manner, a short-distance spray manner, and a long-distance spray manner. In a case in which the emission unit 200 sprays the mixed gas in the contact spray manner, the emission unit 200 may spray the mixed gas using a mask. In a case in which the emission unit 200 sprays the mixed gas in the short-distance spray manner, the emission unit 200 may spray the mixed gas using a user's arm or an external force. In a case in which the emission unit 200 sprays the mixed gas in the long-distance spray manner, the emission unit 200 may spray the mixed gas in a manner in which the gas is sprayed by a humidifier.

Although not illustrated in the drawings, the emission unit 200 may include a temperature and humidity control unit configured to control at least one of a temperature and a humidity of the mixed gas discharged from the emission unit 200. For example, the temperature of the mixed gas discharged from the emission unit 200 may be controlled by, for example, a heating wire. For example, the humidity of the mixed gas discharged from the emission unit 200 may be controlled by a humidifier.

The emission unit 200 may include a flow channel unit 210 for movement of the mixed gas and the spraying unit 220 for spraying of the mixed gas transmitted through the flow channel unit 210.

One end of the flow channel unit 210 may be connected to the storage unit 130, the other end thereof may be connected to the spraying unit 220, and the flow channel unit 210 may move the mixed gas to the spraying unit 220 through a flow channel provided therein. For example, the flow channel unit 210 may include a mixed gas providing tube to move the mixed gas to the spraying unit 220.

The flow channel unit 210 may have a stretchable or shape-changeable structure to control or maintain the preset distance d between the spraying unit 220 and the user's face. Accordingly, a length of the flow channel unit 210 may increase so that a distance between the spraying unit 220 and the user's face decreases and may decrease so that the distance between the spraying unit 220 and the user's face increases.

The spraying unit 220 may be connected to the other end of the flow channel unit 210 and may spray the mixed gas received through the flow channel unit 210 toward the user's face.

The spraying unit 220 may include at least one nozzle 221 through which the mixed gas is sprayed.

The spraying unit 220 is connected to the flow channel unit 210 and is in a non-contact state in which the spraying unit 220 is spaced apart from the user's face by the preset distance d, and sleep may be induced without causing discomfort or displeasure to the user through the spray in the non-contact state.

The sensor unit 300 may include a distance sensing sensor 310, a concentration sensing sensor 320, and a sleeping status detecting sensor 330.

According to one embodiment of the present invention, the distance sensing sensor 310 may be provided at one side of the spraying unit 220.

The distance sensing sensor 310 may measure a distance between the spraying unit 220 and the user's face.

The distance sensing sensor 310 may transmit a signal of the measured distance to the control unit 400, and the control unit 400 may control a length of the flow channel unit 210 so that the distance between the spraying unit 220 and the user's face is within the preset distance d.

In order to induce sleep of the user, the preset distance d between the spraying unit 220 and the user's face may be set to 14 to 21 cm and preferably 17 cm.

The preset distance may be set in consideration that the concentration may be reduced due to diffusion while the mixed gas with the carbon dioxide concentration of 3 to 10% is sprayed and reaches the user's face, the mixed gas may reach the user's face in a state in which the concentration of the carbon dioxide is reduced to the range of 1.5 to 2.5% while moving by the preset distance d, and the user may inhale the mixed gas with a carbon dioxide concentration of 1.5 to 2.5% so that sleep of the user is inducible.

According to one embodiment of the present invention, the concentration sensing sensor 320 may measure the carbon dioxide concentration of the mixed gas sprayed toward the user's face.

The concentration sensing sensor 320 may be provided at one side of the spraying unit 220 or one portion of the flow channel unit 210 to measure the concentration of the carbon dioxide contained in the mixed gas.

The concentration sensing sensor 320 may transmit a signal of the measured carbon dioxide concentration to the control unit 400, and the control unit 400 may control a mixing ratio of the carbon dioxide in the mixing unit 120 on the basis of the signal of the carbon dioxide concentration.

For example, the concentration sensing sensor 320 may measure the carbon dioxide concentration of the mixed gas discharged from spraying unit 220, and in a case in which the measured carbon dioxide concentration is 35,000 ppm or 3.5%, the control unit 400 may maintain the mixing ratio of the carbon dioxide. In a case in which the measured carbon dioxide concentration is less than 35,000 ppm or 3.5%, the control unit 400 may increase the mixing ratio of the carbon dioxide. In a case in which the measured carbon dioxide concentration is greater than 35,000 ppm or 3.5%, the control unit 400 may decrease the mixing ratio of the carbon dioxide.

According to one embodiment of the present invention, the sleeping status detecting sensor 330 may determine whether the user is in a sleep state.

The sleeping status detecting sensor 330 may be a motion sensor for obtaining movement of the user.

The sleeping status detecting sensor 330 may transmit a signal of the movement of the user to the control unit 400, and the control unit 400 may check and determine whether the user sleeps on the basis of the signal of the movement to stop or continue the spray of the mixed gas.

For example, on the basis of the signal of the movement measured by the sleeping status detecting sensor 330, in a case in which the control unit 400 determines that the user is in the sleep state, the control unit 400 may stop the spray of the mixed gas.

Unlike this, whenever the control unit 400 determines that the user is not in the sleep state, the control unit 400 may extend a time of the spray of the mixed gas by five minutes, and a maximum of a total sum of extended spray times is not greater than 30 minutes.

Although not illustrated in the drawings, the sensor unit 300 may further include a biological marker sensor unit capable of checking a biological marker when the user is in the sleep state or in a non-sleep state. For example, the biological marker sensor unit may measure a heart rate, a blood pressure, and the like of the user. The biological marker sensor unit may be a contact or non-contact type biological marker sensor unit. For example, in a case in which the biological marker sensor unit is the contact type biological marker sensor unit, the biological marker sensor unit may be a contact sensor configured to come into contact with the user. For, example, in a case in which the biological marker sensor unit is the non-contact type biological marker sensor unit, the biological marker sensor unit may be a non-contact type radar which does not come into contact with the user.

When the biological marker sensor unit detects a biological marker of the user, the control unit 400 may check a sleep pattern, sleep quality, and the like of the user on the basis of the biological marker of the user. As necessary, the biological marker sensor unit may provide the sleep pattern, sleep quality, and the like of the user to the control unit 400 in conjunction with a camera capable of checking a sleeping status of the user. In this case, the sleep-inducing system 10 using carbon dioxide may further include a camera capable checking a sleeping status of a user.

The control unit 400 may check the sleep pattern, sleep quality, and the like of the user and individually provide feedback to the user on whether it is necessary to visit a hospital.

Although not illustrated in the drawings, the sensor unit 300 may include a voice recognition unit capable of recognizing a voice of a user. For example, when the voice recognition unit recognizes a voice of the user, the control unit 400 may serve a function of concentration control, power-off, power-on, and the like according to the voice of the user. For example, the voice recognition unit may be an artificial intelligent speaker.

Although not illustrated in the drawings, a voice of a first user recognized by the voice recognition unit may be recorded in a voice recorder. The voice of the first user recorded in the voice recorder may be provided to the control unit 400 and may be provided when the first user or a second user sleeps. For example, a parent of a baby may record his or her voice using the voice recognition unit and the voice recorder. The control unit 400 may provide the recorded voice (for example, a lullaby) of the parent of the baby to the baby to help the baby to sleep.

The voice of the first user may be recorded through an external device 50, for example, an application installed in a mobile phone or the like and provided when the first user or second user sleeps.

According to one embodiment of the present invention, the sleep-inducing system 10 using carbon dioxide may further include a purification unit 500.

The purification unit 500 may include solid oxygen (not shown) for removing the carbon dioxide contained in the mixed gas sprayed through the emission unit 200 to decrease the carbon dioxide concentration and a diffusion fan (not shown) for widely spreading the solid oxygen around the user.

When the mixed gas is sprayed through the emission unit 200 for a preset time and the spraying is completed, the control unit 400 may drive the diffusion fan of the purification unit 500 to diffuse the solid oxygen around the user.

Accordingly, the solid oxygen may remove the carbon dioxide with a high concentration which is spread in the atmosphere for inducing sleep of the user.

According to one embodiment of the present invention, the control unit 400 may include a communication unit 410 capable of transmitting and receiving a data signal to and from the external device 50.

The sleep-inducing system 10 using carbon dioxide according to one embodiment of the present invention may transmit and receive the data signal to and from a system or device related to a sleep environment of the user through the communication unit 410. For example, the sleep-inducing system 10 using carbon dioxide according to one embodiment of the present invention may be wirelessly connected to a humidifier, an air conditioner, a curtain, and the like through the communication unit 410. The sleep-inducing system 10 using carbon dioxide according to one embodiment of the present invention may transmit and receive data through the communication unit 410, control the humidifier, air conditioner, curtain, and the like, and thus provide an optimized sleep state to the user.

The control unit 400 may set a range of the carbon dioxide concentration of the mixed gas according to a signal received from the external device 50 and a carbon dioxide concentration according to a distance by which the user's face is spaced apart from the emission unit 200.

Although not illustrated in the drawings, the control unit 400 may determine a concentration of the mixed gas optimized to each user and control the concentration of the mixed gas accordingly. When the concentration, which is optimized to each user, of the mixed gas is determined, the control unit 400 may consider at least one among factors such as gender, age, height, and weight of the user.

The sleep-inducing system 10 using carbon dioxide according to one embodiment of the present invention may generate the mixed gas within the safe concentration range using the mixing unit 120, provide the mixed gas to the user through the emission unit 200, control the concentration to be within the safe concentration range around the user's respiration system, and momentarily increase the carbon dioxide concentration of air inhaled by the user having difficulty in sleeping so that an optimal sleep environment may be provided to the user.

Hereinafter, a sleep-inducing device using carbon dioxide according to one embodiment of the present invention will be described. Hereinafter, a difference from the sleep-inducing system using carbon dioxide according to one embodiment of the present invention will be described more specifically, and contents which are not described may be the same as the contents described when the sleep-inducing system using carbon dioxide according to one embodiment of the present invention has been described.

Figure 4A:
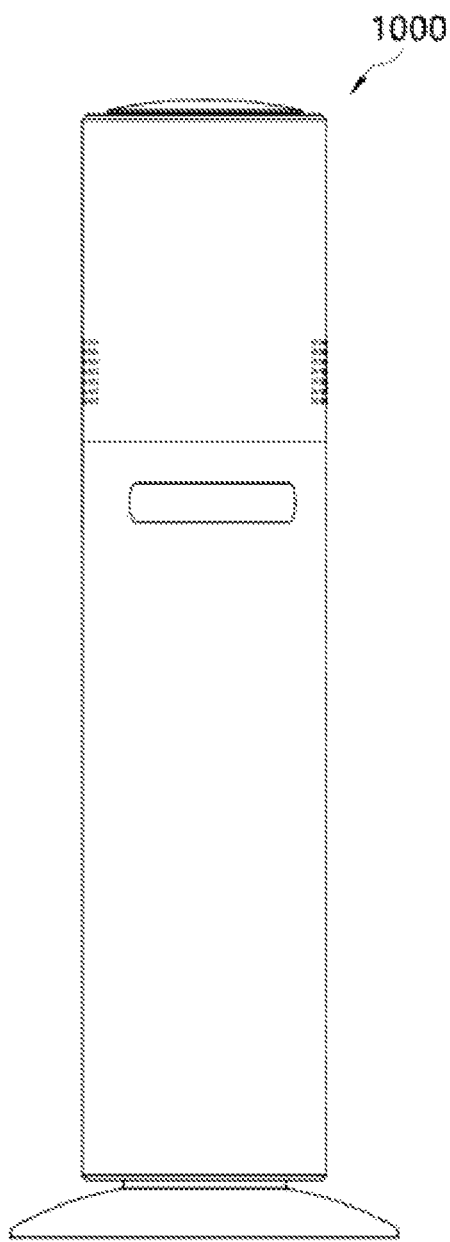
FIG. 4A is a schematic front view illustrating a sleep-inducing device using carbon dioxide according to one embodiment of the present invention.
Figure 4B:
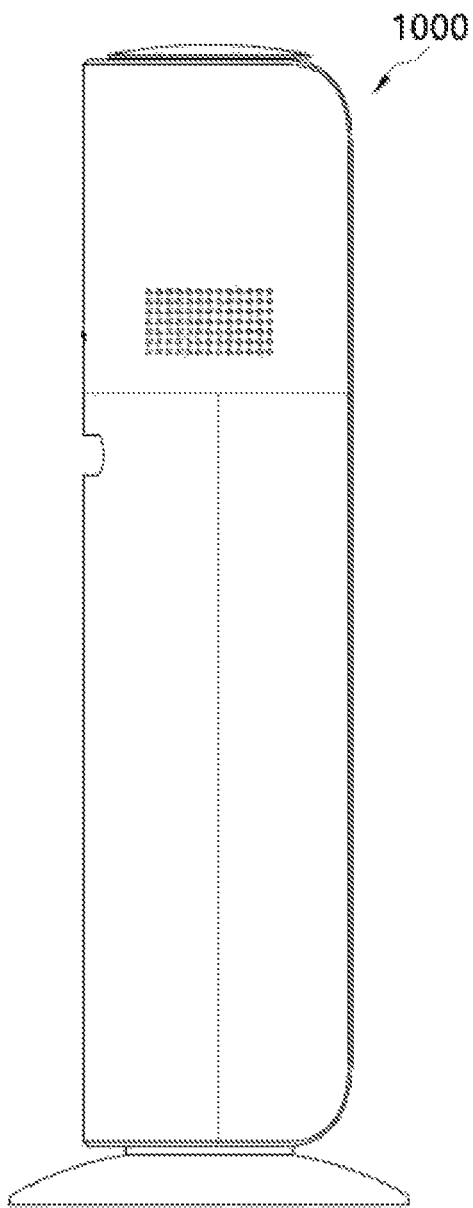
FIG. 4B is a schematic side view illustrating the sleep-inducing device using carbon dioxide according to one embodiment of the present invention.
Figure 4C:
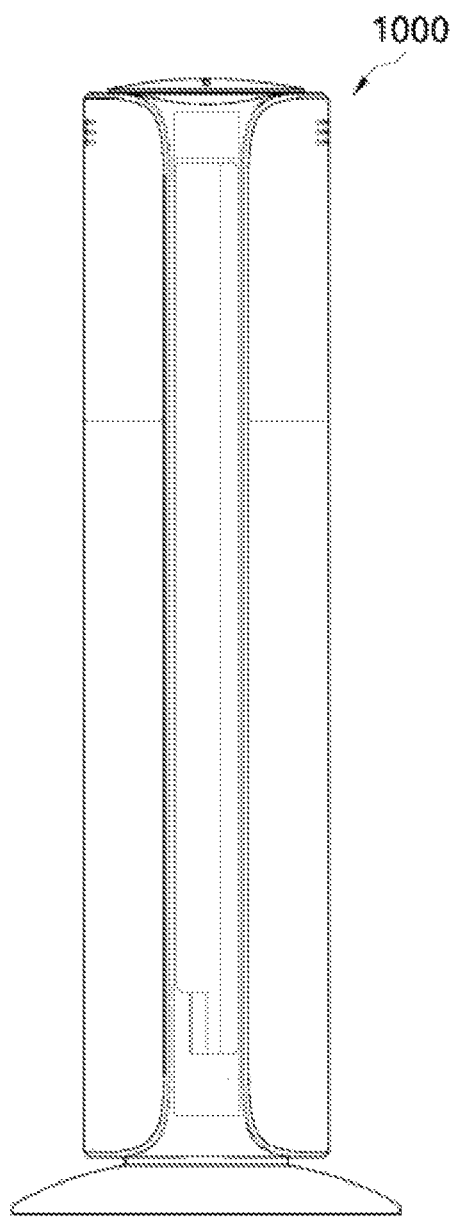
FIG. 4C is a schematic rear view illustrating the sleep-inducing device using carbon dioxide according to one embodiment of the present invention.

FIG. 4A is a schematic front view illustrating a sleep-inducing device using carbon dioxide according to one embodiment of the present invention. FIG. 4B is a schematic side view illustrating the sleep-inducing device using carbon dioxide according to one embodiment of the present invention. FIG. 4C is a schematic rear view illustrating the sleep-inducing device using carbon dioxide according to one embodiment of the present invention.

Figure 5:
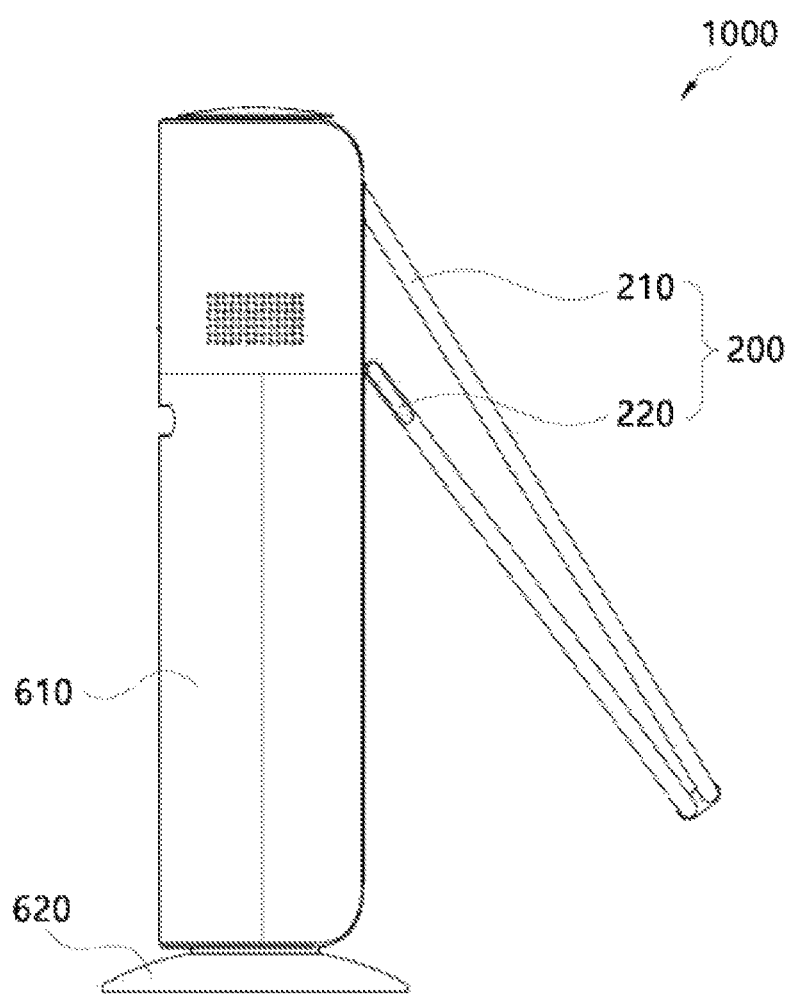
FIGS. 5 and 6 are views sequentially illustrating operations of unfolding a flow channel unit and discharging of a spraying unit of the sleep-inducing device using carbon dioxide according to one embodiment of the present invention.
Figure 6:
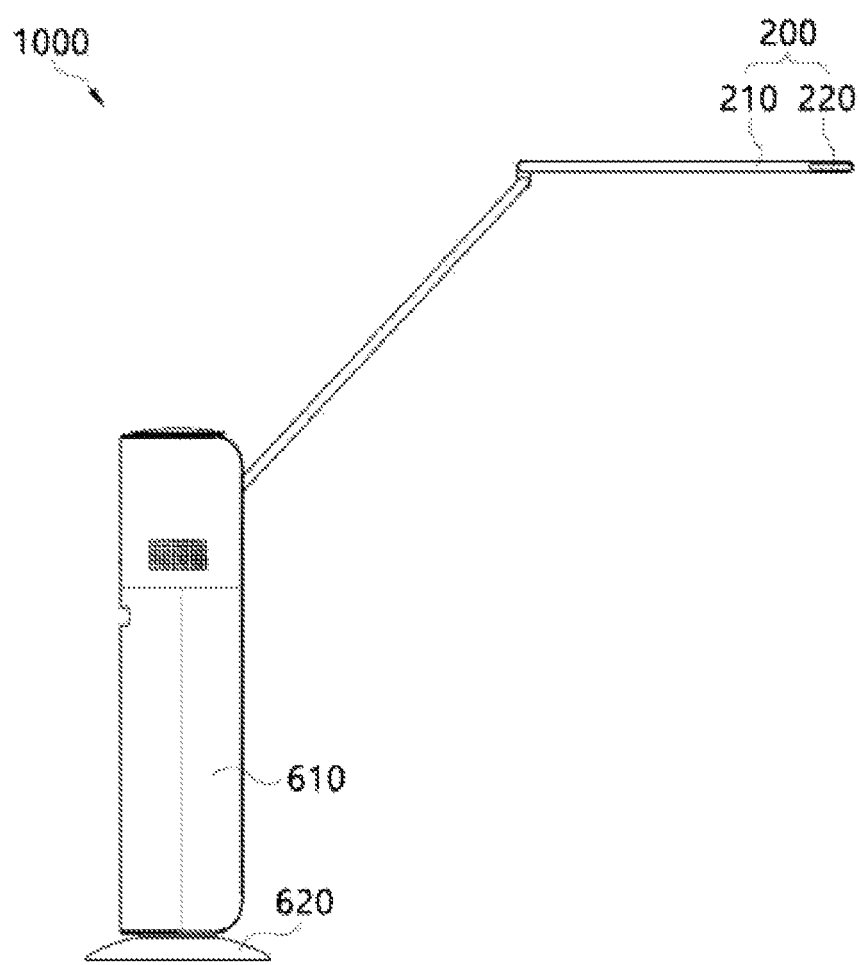

FIGS. 5 and 6 are views sequentially illustrating operations of unfolding a flow channel unit and discharging of a spraying unit of the sleep-inducing device using carbon dioxide according to one embodiment of the present.

Figure 7:
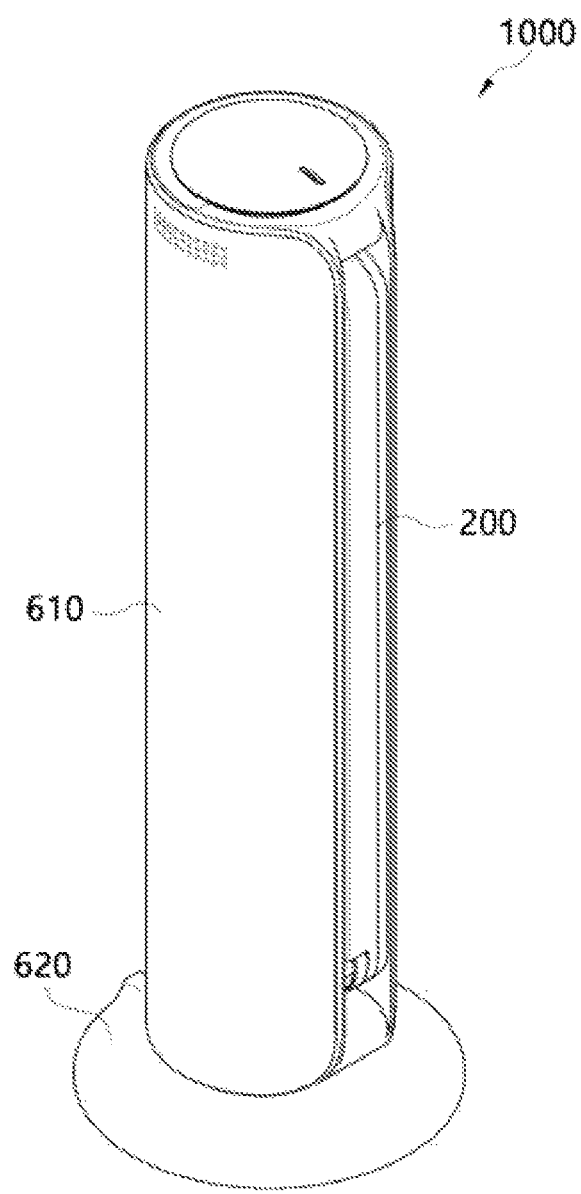
FIG. 7 is a schematic perspective view illustrating the sleep-inducing device using carbon dioxide according to one embodiment of the present invention.
Figure 8:
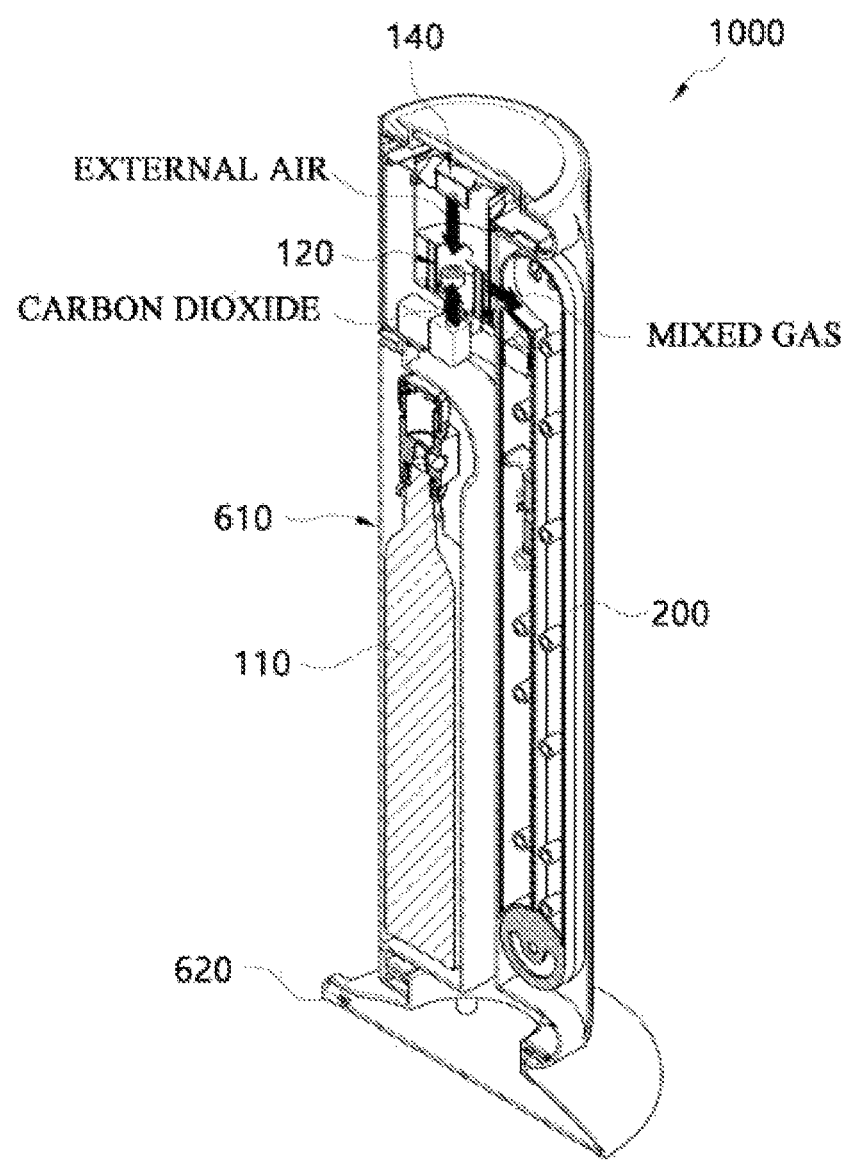
FIG. 8 is a schematic cross-sectional view illustrating the sleep-inducing device using carbon dioxide according to one embodiment of the present invention.

FIG. 7 is a schematic perspective view illustrating the sleep-inducing device using carbon dioxide according to one embodiment of the present invention. FIG. 8 is a schematic cross-sectional view illustrating the sleep-inducing device using carbon dioxide according to one embodiment of the present invention. FIG. 9 is a perspective view in which a portion of a housing is removed from the sleep-inducing device using carbon dioxide according to one embodiment of the present invention to observe an interior thereof.

Referring to FIGS. 1 and 4 to 9, a sleep-inducing device 1000 using carbon dioxide according to one embodiment of the present invention may include a housing 610 and a fixing unit 620. The housing 610 may include the mixed gas generation unit 100. The mixed gas generation unit 100 may mix the provided carbon dioxide ($CO_2$) and air to generate a mixed gas of which a concentration of the carbon dioxide is within a preset range. The mixed gas generation unit 100 will be described in more detail below.

The fixing unit 620 may be connected to the housing 610 to fix the sleep-inducing device 1000 using carbon dioxide. A width of the fixing unit 620 may be greater than a width of the housing 610. However, the present invention is not limited thereto, and the width, shape, and the like of the fixing unit 620 are not particularly limited as long as the sleep-inducing device 100 using carbon dioxide may be fixed.

The housing 610 and the fixing unit 620 are integrally formed. However, the present invention is not limited thereto, and the housing 610 and the fixing unit 620 may be individually formed and coupled to each other.

The sleep-inducing device 1000 using carbon dioxide according to one embodiment of the present invention may include the mixed gas generation unit 100 and the emission unit 200.

The mixed gas generation unit 100 is accommodated in the housing 610. The mixed gas generation unit 100 may include the providing unit 110 and the mixing unit 120. The mixed gas generation unit 100 may include the storage unit 130. The mixed gas generation unit 100 may include an external air inflowing unit 140.

The providing unit 110 may store the carbon dioxide therein and supply the carbon dioxide to the mixing unit 120. The providing unit 110 may be accommodated in the housing 610. The providing unit 110 may be provided under the external air inflowing unit 140 and the mixing unit 120.

The providing unit 110 may include the RFID. Accordingly, it may be determined whether the providing unit 110 is suitable to be used in the sleep-inducing device 1000 using carbon dioxide according to one embodiment of the present invention, for example, whether the providing unit 110 is a genuine product.

The providing unit 110 may exhaust the carbon dioxide stored therein while supplying the carbon dioxide. Accordingly, in a case in which the providing unit 110 is a disposable unit, the providing unit 110 may have a structure detachably or separably connected to the mixing unit 120 so that the providing unit 110 is replaceable. In addition, in a case in which the providing unit 110 is for a rechargeable multi-use unit, the providing unit 110 may have a structure into which carbon dioxide is injectable.

The providing unit 110 may be connected to the mixing unit 120 through the tube 140 for supplying the carbon dioxide, and the valve 145 for controlling a flow rate of the carbon dioxide may be provided on the tube 140 to control opening or closing of the tube 140.

For example, the valve 145 may be a solenoid valve of which opening or closing is electronically controlled by the control unit 400, and the control unit 400 may control an opening degree of the valve 145 to control a flow rate of the carbon dioxide supplied to the mixing unit 120.

The external air inflowing unit 140 receives external air from the outside. The term "outside" may denote an outside of the housing 610. The external air inflowing unit 140 may be provided in, for example, a fan shape in the housing 610. The external air inflowing unit 140 may provide the external air to the mixing unit 120.

The mixing unit 120 may receive the carbon dioxide from the providing unit 110, mix the received carbon dioxide and the external air received from the external air inflowing unit 140 to generate a mixed gas of which a carbon dioxide concentration is within the range of 30,000 to 100,000 ppm or the range of 3 to 10% in the mixing unit and within the range of 15,000 to 25,000 ppm or the range of 1.5 to 2.5% in the user's inhalation system.

The mixing unit 120 may be accommodated in the housing 610. The mixing unit 120 may be provided between the external air inflowing unit 140 and the providing unit 110. The mixing unit 120 is connected to the emission unit 200. The mixing unit 120 may be connected to the flow channel unit 210 to provide mixed air.

The mixing unit 120 may be formed to have a housing structure in which an accommodation space is provided to mix the carbon dioxide and external air. Referring to FIG. 8, the mixing unit 120 may be integrally formed with the storage unit 130. That is, the mixing unit 120 may generate the mixed gas, and the mixed gas may be accommodated or stored.

According to a test result in an autonomous manner, it was seen that, in a case in which a concentration of the carbon dioxide in air is within the range of 1.5 to 2.5% in the user's inhalation system, drowsiness of the user is induced so that sleeping may be induced.

According to one embodiment of the present invention, the mixed gas of which the concentration of the carbon dioxide is within the range of 30,000 to 100,000 ppm or the range of 3 to 10% in the mixing unit 120 is generated in consideration that the concentration may be reduced due to diffusion in a process in which the mixed gas is provided to or sprayed onto the user's face, and thus the mixed gas of which a carbon dioxide concentration is within the range of 1.5 to 2.5 may be provided to the user's face spaced apart from the spraying unit 220 by 14 to 21 cm.

The sleep-inducing device 1000 using carbon dioxide according to one embodiment of the present invention generates the mixed gas within the range of TWA-5,000/STEL-30,000 which is a carbon dioxide exposure safety concentration (hereinafter, "safety concentration") specified by the U.S. Occupational Safety and Health Administration and governments around the world including the Republic of Korea. The term "TWA-5,000" denotes that the exposure time should be less than or equal to eight hours at an average of 5,000 ppm or less, and the term "STEL-30,000" denotes that the exposure time should be less than or equal to 15 minutes at 30,000 ppm.

That is, the mixing unit 120 of the sleep-inducing device 1000 using carbon dioxide according to one embodiment of the present invention generates the mixed gas within the safe concentration range. In addition, the sleep-inducing device 1000 using carbon dioxide according to one embodiment of the present invention may provide the mixed gas to the user through the emission unit 200 to control the concentration around a user's respiration system to be within the safe concentration range and also provide an optimized sleep environment to the user.

The emission unit 200 may spray the mixed gas from a position spaced apart from the user's face by a preset distance d. For example, the emission unit 200 may spray the mixed gas onto the user's face in at least one manner among a contact spray manner, a short-distance spray manner, and a long-distance spray manner. In a case in which the emission unit 200 sprays the mixed gas in the contact spray manner, the emission unit 200 may spray the mixed gas using a mask. In a case in which the emission unit 200 sprays the mixed gas in the short-distance spray manner, the emission unit 200 may spray the mixed gas using the user's arm or an external force. In a case in which the emission unit 200 sprays the mixed gas in the long-distance spray manner, the emission unit 200 may spray the mixed gas in a manner in which the gas is sprayed by a humidifier.

Although not illustrated in the drawings, the emission unit 200 may include the temperature and humidity control unit configured to control at least one of a temperature and a humidity of the mixed gas discharged from the emission unit 200. For example, the temperature of the mixed gas discharged from the emission unit 200 may be controlled by, for example, a heating wire. For example, the humidity of the mixed gas discharged from the emission unit 200 may be controlled by a humidifier.

The emission unit 200 may include the flow channel unit 210 for movement of the mixed gas and the spraying unit 220 for spray of the mixed gas transmitted through the flow channel unit 210.

The flow channel unit 210 may have a stretchable or shape-changeable structure to control or maintain the preset distance d between the spraying unit 220 and the user's face. Referring to FIGS. 5 and 6, the flow channel unit 210 may be bent through a hinge. In FIGS. 5 to 6, it is illustrated that the flow channel unit 210 is bent, for example, one time, but the flow channel unit 210 may be bent a plurality of times which is two or more times.

For example, when the user does not use the sleep-inducing device 1000 using carbon dioxide, the flow channel unit 210 may be bent and accommodated in a side portion of the housing 610 to reduce an occupying space. For example, when the user uses the sleep-inducing device 1000 using carbon dioxide, the flow channel unit 210 may be spaced apart from the side portion of the housing 610 and used in a shape illustrated in FIG. 6. In this case, a distance between the spraying unit 220 and the user's face may be set by adjusting a position of the flow channel unit 210.

One end of the flow channel unit 210 may be connected to the mixing unit 120, and the other end thereof may be connected to the spraying unit 220 to move the mixed gas to the spraying unit 220 through a flow channel provided therein. For example, the flow channel unit 210 may include the mixed gas providing tube therein to move the mixed gas to the spraying unit 220.

The spraying unit 220 may be connected to the other end of the flow channel unit 210 and may spray the mixed gas received through the flow channel unit 210 toward the user's face.

The spraying unit 220 may include at least one nozzle 221 through which the mixed gas is sprayed.

The spraying unit 220 is connected to the flow channel unit 210 and is in a non-contact state in which the spraying unit 220 is spaced apart from the user's face by the preset distance d, and sleep may be induced without causing discomfort or displeasure to the user by spraying in the non-contact state.

The sleep-inducing device 1000 using carbon dioxide according to one embodiment of the present invention may include the sensor unit 300 and the control unit 400.

The sensor unit 300 may include the distance sensing sensor 310, the concentration sensing sensor 320, and the sleeping status detecting sensor 330.

For example, the spraying unit 220 may be provided at one side of the flow channel unit 210, and the sensor unit 300 may be provided at the other side of the flow channel unit 210.

Although not illustrated in the drawings, the sensor unit 300 may further include the biological marker sensor unit capable of checking a biological marker when the user is in a sleep state or in a non-sleep state. For example, the biological marker sensor unit may measure a heart rate, a blood pressure, and the like of the user. The biological marker sensor unit may be a contact or non-contact type biological marker sensor unit. For example, in a case in which the biological marker sensor unit is the contact type biological marker sensor unit, the biological marker sensor unit may be a contact sensor configured to come into contact with the user. For example, in a case in which the biological marker sensor unit is the non-contact type biological marker sensor unit, the biological marker sensor unit may be a non-contact type radar which does not come into contact with the user.

When the biological marker sensor unit detects a biological marker of the user, the control unit 400 may check a sleep pattern, sleep quality, and the like of the user on the basis of the biological marker of the user. As necessary, the biological marker sensor unit may provide the sleep pattern, sleep quality, and the like of the user to the control unit 400 in conjunction with a camera capable of checking a sleeping status of the user. In this case, the sleep-inducing system 1000 using carbon dioxide may further include the camera capable of checking the sleeping status of the user.

The control unit 400 may check the sleep pattern, sleep quality, and the like of the user and individually provide feedback to the user on whether it is necessary to visit a hospital.

Although not illustrated in the drawings, the sensor unit 300 may include the voice recognition unit capable of recognizing a voice of a user. For example, when the voice recognition unit recognizes a voice of the user, the control unit 400 may serve a function of concentration control, power-off, power-on, and the like according to the voice of the user. For example, the voice recognition unit may be an artificial intelligent speaker.

Although not illustrated in the drawings, a voice of a first user recognized by the voice recognition unit may be recorded in a voice recorder. The voice of the first user recorded in the voice recorder may be provided to the control unit 400 and may be provided when the first user or a second user sleep. For example, a parent of a baby may record his or her voice using the voice recognition unit and the voice recorder. The control unit 400 may provide the recorded voice (for example, a lullaby) of the parent of the baby to the baby to help sleep of the baby.

The voice of the first user may be recorded through an external device 50, for example, an application installed in a mobile phone or the like and provided when the first user or second user sleeps.

The control unit 400 controls the carbon dioxide concentration of the mixed gas generated by the mixed gas generation unit 100 to be within a preset range on the basis of the measured carbon dioxide concentration.

Although not illustrated in the drawings, the control unit 400 may determine a concentration of the mixed gas optimized to each user and control the concentration of the mixed gas accordingly. When the concentration, which is optimized to each user, of the mixed gas is determined, the control unit 400 may consider at least one among factors such as gender, age, height, and weight of the user.

The sleep-inducing device 1000 using carbon dioxide according to one embodiment of the present invention may generate the mixed gas within the safe concentration range using the mixing unit 120, provide the mixed gas to the user through the emission unit 200, control the concentration to be within the safe concentration range around the user's respiration system, and momentarily increase the carbon dioxide concentration of air inhaled by the user having difficulty in sleeping so that an optimal sleep environment may be provided to the user.

While the exemplary embodiments of the present invention have been described in detail as described above, the present invention is not limited thereto and may be variously changed within the range of claims, the mode of invention, and the accompanying drawings, and such changes also naturally fall within the present invention.

The invention claimed is:

1. A sleep-inducing system using carbon dioxide comprising:
   a mixed gas generation unit configured to receive both an external air and a carbon dioxide such that a mixed gas is generated;
   an emission unit configured to provide the mixed gas to atmosphere at a place distanced from a target, wherein the emission unit is distanced from the target by 14 cm or more when the mixed gas is provided to the target;
   a distance sensing sensor configured to obtain a distance between the target and the emission unit; and
   a control unit configured to:
     receive the obtained distance, and
     control a concentration of carbon dioxide in the mixed gas which is provided to atmosphere within a range from 30,000 ppm to 100,000 ppm,
     wherein the control unit is configured to control the concentration in a first concentration when the obtained distance is a first distance and
     wherein the control unit is configured to control the concentration in a second concentration larger than the first concentration when the obtained distance is a second distance larger than the first distance,
     whereby a concentration of carbon dioxide at the target distanced from the emission unit can be controlled within a range from 15,000 ppm to 25,000 ppm.

2. The sleep-inducing system using carbon dioxide of claim 1, wherein,
   the mixed gas generation unit comprises:
   a providing unit configured to store the carbon dioxide; and
   a mixing unit configured to receive both the carbon dioxide and the external air such that the mixed gas is generated, wherein the providing unit is configured to provide the carbon dioxide to the mixing unit;

wherein the control unit is configured to control a flow rate of carbon dioxide provided from the providing unit to the mixing unit or controls a flow rate of the external air from outside such that the concentration of carbon dioxide in the mixed air can be controlled.

3. The sleep-inducing system using carbon dioxide of claim 2, wherein,
the providing unit is a disposable gas tank.

4. The sleep-inducing system using carbon dioxide of claim 1, wherein,
the emission unit comprises an outlet for the mixed gas and a flow channel between the mixed gas generation unit and the outlet, wherein the flow channel is configured to provide a pathway for the mixed gas, and
wherein the flow channel is stretchable or shape-changeable such that a distance between the emission unit and the target is changeable.

5. The sleep-inducing system using carbon dioxide of claim 4, further comprising a concentration sensing sensor configured to measure a concentration of carbon dioxide, and
wherein the concentration sensing sensor is located adjacent to the outlet of the emission unit.

6. The sleep-inducing system using carbon dioxide of claim 1, further comprising:
a sleeping status detecting sensor configured to detect the sleeping status of a subject;
wherein the sleeping status detecting sensor detects the sleeping status after emission of the mixed gas for a preset time and
wherein the control unit is configured to receive the sleeping status detection signal and control the emission of the mixed gas based on the sleeping status detection signal, and
wherein the control unit is configured to terminate the emission of the mixed gas when the subject is in sleeping status, and continue the emission of the mixed gas for a predetermined period when the subject is not in a sleeping status.

7. The sleep-inducing system using carbon dioxide of claim 1, further comprising:
a purification unit configured to store a solid oxygen for lowering the concentration of the carbon dioxide in the mixed gas, wherein the purification unit comprises a diffusion fan for spreading the oxygen widely around, and
wherein when the emission of the mixed gas is terminated, the control unit is configured to control an operation of the diffusion fan of the purification unit to spread the solid oxygen toward the target.

8. The sleep-inducing system using carbon dioxide of claim 1, wherein,
the control unit further comprises a communication unit configured to transmit data signal to an external device and receive data signal from the external device, and
wherein the control unit is configured to control a concentration of carbon dioxide in the mixed gas based on the data signal received from the external device.

9. The sleep-inducing system using carbon dioxide of claim 1, wherein the sleep-inducing system has no part which contacts with the target when the emission unit provides the mixed gas to the target.

10. A sleep-inducing device using carbon dioxide comprising:
an external air inflowing unit configured to receive external air from an outside of the sleep-inducing device and provide the external air to an inside of the sleep-inducing device;
a providing unit located adjacent to the external air inflowing unit and configured to provide carbon dioxide;
a mixing unit configured to receive both the external air and the carbon dioxide such that a mixed gas is generated;
an emission unit connected with the mixing unit and configured to receive the mixed gas from the mixing unit and provide the mixed gas to atmosphere at a location distanced from a target, wherein the emission unit is distanced from the target by 14 cm or more when the mixed gas is provided to the target; and
a distance sensing sensor configured to obtain a distance between the emission unit and the target, and
a control unit configured to:
receive the obtained distance, and
control a concentration of carbon dioxide in the mixed gas which is provided to atmosphere within a range from 30,000 ppm to 100,000 ppm,
wherein the control unit is configured to control the concentration in a first concentration when the obtained distance is a first distance and
wherein the control unit is configured to control the concentration in a second concentration larger than the first concentration when the obtained distance is a second distance larger than the first distance,
whereby a concentration of carbon dioxide at the target distanced from the emission unit can be controlled within a range from 15,000 ppm to 25,000 ppm.

11. The sleep-inducing device using carbon dioxide of claim 10, wherein,
the providing unit is a disposable gas tank.

12. The sleep-inducing device using carbon dioxide of claim 10, wherein,
the emission unit comprises an outlet for the mixed gas and a flow channel between the mixed gas generation unit and the outlet, wherein the flow channel is configured to provide a pathway for the mixed gas.

13. The sleep-inducing device using carbon dioxide of claim 12, wherein,
the flow channel is stretchable or shape-changeable such that a distance between the emission unit and the target is changeable.

14. The sleep-inducing device using carbon dioxide of claim 10, wherein the sleep-inducing system has no part which contacts with the target when the emission unit provides the mixed gas to the target.

* * * * *